(12) United States Patent
Björk et al.

(10) Patent No.: US 6,642,249 B2
(45) Date of Patent: Nov. 4, 2003

(54) IMMUNOMODULATING COMPOUNDS

(75) Inventors: Per Axel Björk, Helsingborg (SE); Tomas Fex, Lund (SE); Lars Olof Göran Pettersson, Södra Sandby (SE); Pous Sørensen, Köpenhamn (DK); Dorthe Da Graça Thrige, Valby (DK)

(73) Assignee: Active Biotech AB, Lund (SE)

( * ) Notice: Subject to any disclaimer, the term of this patent is extended or adjusted under 35 U.S.C. 154(b) by 0 days.

(21) Appl. No.: 10/179,731

(22) Filed: Jun. 26, 2002

(65) Prior Publication Data

US 2003/0022913 A1 Jan. 30, 2003

Related U.S. Application Data

(60) Provisional application No. 60/302,666, filed on Jul. 5, 2001.

(30) Foreign Application Priority Data

Jul. 4, 2001 (SE) ............................................. 0102404

(51) Int. Cl.$^7$ ................ A61K 31/4745; A61K 31/4162; C07D 471/04; C07D 491/052; C07D 495/04; A61P 37/00
(52) U.S. Cl. .......................... 514/293; 514/405; 546/82; 548/359.5
(58) Field of Search ........................ 546/82; 548/359.5; 514/293, 405

(56) References Cited

U.S. PATENT DOCUMENTS

| | | | |
|---|---|---|---|
| 4,268,516 A | 5/1981 | Lombardino et al. | |
| 4,312,870 A | 1/1982 | Yokoyama | |

FOREIGN PATENT DOCUMENTS

| | | |
|---|---|---|
| EP | 0354693 A1 | 2/1990 |
| EP | 0354694 A1 | 2/1990 |
| WO | 91/06298 A1 | 5/1991 |
| WO | 91/11448 A1 | 8/1991 |
| WO | 97/34893 A1 | 9/1997 |

OTHER PUBLICATIONS

Novel Preparation of 1–Aryl–3–(2–hydroxyphenyl)–2–pyrazolin–5–ones and their Conversion into 2–Aryl–4–methyl[1]benzopyrano[4,3–c]pyrazol–3(2H)–ones, Jayne A. Froggett, et al., Knoll Pharmaceuticals Research and Development Department, Pennyfoot Street, Nottingham NG1 1GF, UK, J. Chem. Research (S), 1997, pp. 30 to 31.
Organolead–mediated Arylation of Allyl β–Ketoesters: A Selective Synthesis of Isoflavanones and Isoflavones, Dervilla M. X. Donnelly, et al., Department of Chemistry, University College Dublin, Belfield, Dublin 4, Ireland, Laboratoire SREP, 'Radicaux Libres et Synthèsé, URA–CNRS 1412, Universitéde Provence, Centre St Jèrôme, 13397 Marseille Cedex 20, France, J. Chem. Soc. Perkin Trans., 1993, pp. 1729 to 1735.

Communications, Reactions of 4–Oxo–4H–1–benzopran–3–carboxylic Acids with Phenylhydrazine, Guanidine, and Hydroxylamine, C.K. Ghosh, et al., Organic Chemistry Laboratory, Department of Biochemistry, Calcutta University, Calcutta 700019, India, Oct. 1978, pp. 779 to 781.

Synthesis and Adenosine Receptor Affinity of a Series of Pyrazolo[3,4–d]pyrimidine Analogues of 1–Methylisoguanosine, Fiona S. Harden, et al., Division of Science and Technology, Griffith University, Brisbane, Queensland 4111, Australia, Received Apr. 15, 1991, J. Med., Chem., 1991, 34, pp. 2892 to 2898.

The Preparation of Substituted Hydrazines, IV. Arylhydrazines via Conventional Methods, I. Moyer Hunsberger et al., Received Oct. 20, 1955, Contribution from the Department of Chemistry, Antioch College, pp. 394 to 399.

Novel Immunosuppressive Agents, Potent Immunological Activity of Some Benzothiopyrano[4,3–c]pyrazol–3–ones, Joseph G. Lombardino, et al., Pfizer Central Research, Pfizer Inc., Groton, Connecticut 06340, Received Dec. 4, 1980, J. Med., Chem. 1981, 24, pp. 830 to 834.

High Affinity Central Benzodiazepine Receptor Ligands: Synthesis and Structure—Activity Relationship Studies of a New Series of Pyrazolo[4,3–c]quinolin–3–ones, L. Savini, et al., Italy, Received Jul. 17, 1997; accepted Oct. 18, 1997, Bioorganic & Medicinal Chemistry 6 (1998), pp. 389 to 399.

CD28/B7 System of T Cell Costimulation, Deborah J. Lenschow, et al., Committee on Immunology, Ben May Institute and the Department of Pathology, University of Chicago, Chicago, Illinois 60637, Annu. Rev. Immunol. 1996, 14, pp. 233 to 258.

*Primary Examiner*—Evelyn Mei Huang
(74) *Attorney, Agent, or Firm*—Burns, Doane, Swecker & Mathis, L.L.P.

(57) ABSTRACT

The present invention relates to a novel heterocyclic compound, a pharmaceutical composition comprisining said compound, a method and use of said compound for clinical treatment of medical conditions which may benefit from immunomodulation, e.g. rheumatoid arthritis, multiple sclerosis, diabetes, asthma, transplantation, systemic lupus erythematosis and psoriasis. More particularly the present invention relates to novel heterocyclic compounds, which are CD80 antagonists capable of inhibiting the interactions between CD80 and CD28. A method of screening compounds for their ability of inhibiting ligand-induced co-stimulatory receptor internalization pathways in immune competent human cells is described. Said immune competent human cells are incubated at conditions capable of inducing co-stimulatory receptor internalization in the presence of at least one test compound and the suppression of the ligand-induced co-stimulatory receptor internalization determined. There is also described a kit for use in such a method, as well as an immunoregulatory drug capable of blocking down-modulation of a ligand-induced receptor.

22 Claims, No Drawings

IMMUNOMODULATING COMPOUNDS

Priority is claimed under 35 U.S.C. §119(a) for Swedish Application No. 0102404-1 filed Jul. 4, 2001, and under 35 U.S.C. §119(e) for U.S. Provisional Application No. 60/302,666 filed Jul. 5, 2001, the entire contents of which are incorporated by reference.

FIELD OF THE INVENTION

The present invention relates to immunomodulating compounds, pharmaceutical compositions comprising said compounds, use of said compound as well as a method for treatment of medical conditions which benefit from immunomodulation, wherein said compounds are administered.

BACKGROUND OF THE INVENTION

The immune system possesses the ability to control the homeostasis between the activation and inactivation of lymphocytes through various regulatory mechanisms during and after an immune response. Among these are mechanisms that specifically inhibit and/or turn off an immune response. Thus, when an antigen is presented by MHC molecules to the T-cell receptor, the T-cells become properly activated only in the presence of additional co-stimulatory signals. In the absence of accessory signals there is no lymphocyte activation and either a state of functional inactivation termed anergy or tolerance is induced, or the T-cell is specifically deleted by apoptosis.

One such co-stimulatory signal involves interaction of CD80 on specialised antigen-presenting cells with CD28 on T-cells, which has been demonstrated to be essential for full T-cell activation. (Lenschow et al. (1996) Annu. Rev. Immunol., 14, 233–258).

PRIOR ART

In U.S. Pat. No. 4,312,870 compound A is disclosed as one of several psychoactive compounds but without any biological data. Some related compounds are described by A. Carotti in Bioorganic & Medicinal Chemistry 6 (1998) 389–399, and from data related to these compounds it is obvious that the carboxylic acid substituent greatly diminishes biologic activity measured as affinity for the CNS benzodiazepine receptor.

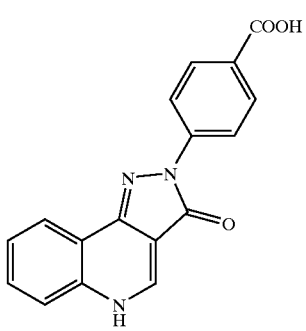

A

EP 0354693A1 (Boots) discloses immunomodulatory compounds of general structure B but does not include structures wherein R7 and/or R8 are COOH or contain a COOH group.

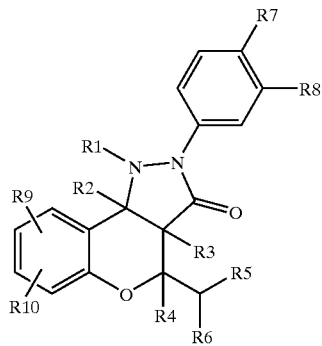

B

Similarly EP 0354694A1 (Boots) discloses immunomodulatory compounds of general structure C but no structures wherein R6 and/or R7 are COOH or contain a COOH group are described.

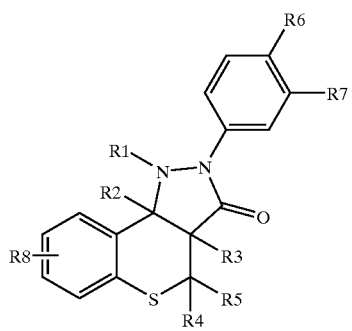

C

Also, WO9111448 (Boots) discloses immunomodulatory compounds of general structure D but here are no structures wherein R7 and/or R8 and R8' are COOH or contain a COOH group.

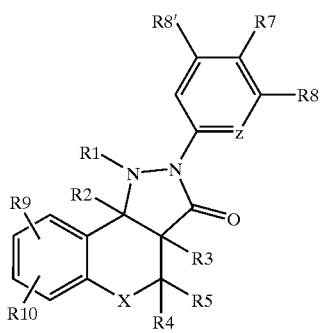

D

SUMMARY OF THE INVENTION

The present invention relates in a first aspect to a novel compound having the general formula (I)

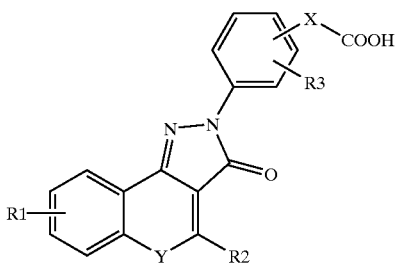

(I)

wherein X represents a bond or a group selected from substituted or unsubstituted $C_{1-3}$-alkyl, NH—C(O)—$C_{1-3}$-alkyl, NH—C(O)—$CH_2$—O—$CH_2$ or C(O)—NH— (amino acid residue);

Y represents NR4, O or S;

R1 represents H, halo, $CF_3$, lower alkyl or lower alkoxy;

R2 and R4 represents independently H or lower alkyl; and

R3 represents H, halo, lower alkyl or lower alkoxy, wherein halo is F, Cl or Br;

wherein lower alkyl represents saturated or unsaturated, straight, branched or cyclic alkyl groups having 1–6 carbon atoms; and wherein lower alkoxy represents saturated or unsaturated, straight, branched or cyclic alkoxy groups having 1–6 carbon atoms, with the proviso that R2 is not H, when X is a bond and Y is NH and R3 is H, or pharmaceutically acceptable salts thereof.

In one preferred embodiment of the invention the compound X is a bond and in another preferred embodiment Y is NH.

In further embodiments the compound is selected from the group comprising

{[3-(3-Oxo-3,5-dihydro-pyrazolo[4,3-c]quinolin-2-yl)-phenylcarbamoyl]-methoxy}-acetic acid, N-[4-(3-Oxo-3,5-dihydro-pyrazolo[4,3-c]quinolin-2-yl)-phenyl]-succinamic acid, 4-[4-(3-Oxo-3,5-dihydro-pyrazolo[4,3-c]quinolin-2-yl)-phenylcarbamoyl]-butyric acid, {[4-(3-Oxo-3,5-dihydro-pyrazolo[4,3-c]quinolin-2-yl)-phenylcarbamoyl]-methoxy}-acetic acid, 4-[4-(3-Oxo-3,5-dihydro-pyrazolo[4,3-c]quinolin-2-yl)-phenylcarbamoyl]-2-phenyl-butyric acid, N-[3-(3-Oxo-3,5-dihydro-pyrazolo[4,3-c]quinolin-2-yl)-phenyl]-succinamic acid, 2-{[4-(3-Oxo-3,5-dihydro-pyrazolo[4,3-c]quinolin-2-yl)-phenylcarbamoyl]-methyl}-benzoic acid, 2-Chloro-4-(3-oxo-3,5-dihydro-pyrazolo[4,3-c]quinolin-2-yl)-benzoic acid, 4-(6,8-Dimethyl-3-oxo-3,5-dihydro-pyrazolo[4,3-c]quinolin-2-yl)-benzoic acid, 4-(8-Methoxy-6-methyl-3-oxo-3,5-dihydro-pyrazolo[4,3-c]quinolin-2-yl)-benzoic acid, 4-(6,8-Dimethoxy-3-oxo-3,5-dihydro-pyrazolo[4,3-c]quinolin-2-yl)-benzoic acid, 4-(7,9-Dimethoxy-3-oxo-3,5-dihydro-pyrazolo[4,3-c]quinolin-2-yl)-benzoic acid, 4-(6-Methyl-3-oxo-8-trifluoromethyl-3,5-dihydro-pyrazolo[4,3-c]quinolin-2-yl)-benzoic acid, 4-(7,9-Dichloro-3-oxo-3,5-dihydro-pyrazolo[4,3-c]quinolin-2-yl)-benzoic acid,

[4-(3-Oxo-3,5-dihydro-pyrazolo[4,3-c]quinolin-2-yl)-phenyl]-propionic acid,

[4-(3-Oxo-3,5-dihydro-pyrazolo[4,3-c]quinolin-2-yl)-phenyl]-acetic acid, 4-(4-Methyl-3-oxo-3H-chromeno[4,3-c]pyrazol-2-yl)-benzoic acid, 4-(3-Oxo-3H-thiochromeno[4,3-c]pyrazol-2-yl)benzoic acid, 4-(5-Methyl-3-oxo-3,5-dihydro-pyrazolo[4,3-c]quinolin-2-yl)-benzoic acid, 2-[4-(3-Oxo-3,5-dihydro-pyrazolo[4,3-c]quinolin-2-yl)-benzoylamino]-3-phenyl-propionic acid, and 2-[4-(3-Oxo-3,5-dihydro-pyrazolo[4,3-c]quinolin-2-yl)-benzoylamino]-2-acetic acid.

In yet another embodiment said compound is a CD80 antagonist, capable of inhibiting the interaction between CD80 and CD28.

The present invention relates in a second aspect to a compound as set forth above for use as a medicament.

In one preferred embodiment said compound is used as a medicament for treatment of medical conditions chosen from the group comprising rheumatoid arthritis, multiple sclerosis, diabetes, asthma, transplantation, systemic lupus erythematosis and psoriasis.

The present invention relates in a third aspect to a compound as set forth above for use as a prodrug, preferably in the form of an ester.

The present invention relates in a fourth aspect to a pharmaceutical composition comprising said compound as active ingredient in association with a pharmaceutically acceptable adjuvant, diluent or carrier.

In one prefered embodiment said pharmaceutical composition is used for treatment of medical conditions chosen from the group comprising rheumatoid arthritis, multiple sclerosis, diabetes, asthma, transplantation, systemic lupus erythematosis and psoriasis.

The present invention relates in a fifth aspect to the use of a compound having the general formula (I)

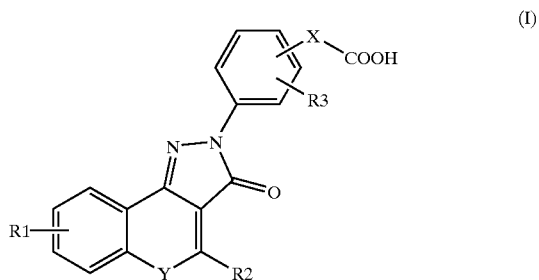

(I)

wherein X represents a bond or a group selected from substituted or unsubstituted $C_{1-3}$-alkyl, NH—C(O)—$C_{1-3}$-alkyl, NH—C(O)—$CH_2$—O—$CH_2$ or C(O)—NH— (amino acid residue);

Y represents NR4, O or S;

R1 represents H, halo, $CF_3$, lower alkyl or lower alkoxy;

R2 and R4 represents independently H or lower alkyl; and

R3 represents H, halo, lower alkyl or lower alkoxy, wherein halo is F, Cl or Br;

wherein lower alkyl represents saturated or unsaturated, straight, branched or cyclic alkyl groups having 1–6 carbon atoms; and wherein lower alkoxy represents saturated or unsaturated, straight, branched or cyclic alkoxy groups having 1–6 carbon atoms, or pharmaceutically acceptable salts thereof, for the manufacture of a medicament for treatment of medical conditions which benefit from immunomodulation.

In one embodiment said medical conditions are chosen from the group comprising rheumatoid arthritis, multiple sclerosis, diabetes, asthma, transplantation, systemic lupus erythematosis and psoriasis.

The present invention relates in a sixth aspect to a method for treatment of medical conditions which benefit from immunomodulation comprising administration of a therapeutically effective amount of a compound having the general formula (I)

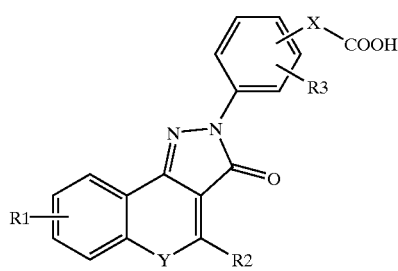

wherein X represents a bond or a group selected from substituted or unsubstituted $C_{1-3}$-alkyl, NH—C(O)—$C_{1-3}$-alkyl, NH—C(O)—$CH_2$—O—$CH_2$ or C(O)—NH— (amino acid residue);

Y represents NR4, O or S;

R1 represents H, halo, $CF_3$, lower alkyl or lower alkoxy;

R2 and R4 represents independently H or lower alkyl; and

R3 represents H, halo, lower alkyl or lower alkoxy, wherein halo is F, Cl or Br;

wherein lower alkyl represents saturated or unsaturated, straight, branched or cyclic alkyl groups having 1–6 carbon atoms; and wherein lower alkoxy represents saturated or unsaturated, straight, branched or cyclic alkoxy groups having 1–6 carbon atoms, or pharmaceutically acceptable salts thereof.

In one embodiment said medical conditions are chosen from the group comprising rheumatoid arthritis, multiple sclerosis, diabetes, asthma, transplantation, systemic lupus erythematosis and psoriasis.

In another embodiment said therapeutically effective amount per day is within the range of 0.001–10 mg/kg body weight, preferably within the range of 0.1–5 mg/kg body weight.

DETAILED DESCRIPTION OF THE INVENTION

The present invention relates to heterocyclic compounds, to pharmaceutical compositions comprising them, and to methods and use of said compounds for clinical treatment of medical conditions which may benefit from immunomodulation, e.g. rheumatoid arthritis, multiple sclerosis, diabetes, asthma, transplantation, systemic lupus erythematosis and psoriasis. More particularly the present invention relates to heterocyclic compounds, which are CD80 antagonists capable of inhibiting the interactions between CD80 and CD28.

According to the present invention it has been found that compounds of general formula I are CD80 antagonists.

Compounds of the general formula I inhibit the interaction between CD80 and CD28. The CD80 antagonistic properties of the compounds of general formula I have been established in Surface Plasmon Resonance (BIAcore) experiments.

It is preferred that X in the general formula I is a bond and in such cases other substituents, such as an adjacent meta-chloro, improves activity.

The compounds of the present invention may be in the acid form but may also be in the form of pharmaceutically acceptable salts.

The compounds of the present invention may also be in the form of prodrugs, especially esters with appropriate alcohols. Prodrugs can have improved pharmacokinetic and/or solubility properties.

Since the compounds of formula I are CD80 antagonists capable of interfering with the CD80–CD28 interaction they are useful for treatment of inflammatory conditions and autoimmune diseases, e.g. rheumatoid arthritis, multiple sclerosis, diabetes, asthma, transplantation, systemic lupus erythematosis and psoriasis.

Effective quantities of the compounds of formula I are preferably administered to a patient in need of such treatment according to usual routes of administration and formulated in usual pharmaceutical compositions comprising an effective amount of the active ingredient and a suitable pharmaceutically acceptable carrier. Such compositions may take a variety of forms, e.g. solutions, suspensions, emulsions, tablets, capsules and powders prepared for oral administration, sterile solutions for parenteral administration, suppositories for rectal administration or suitable topical formulations. Conventional procedures for the selection and preparation of suitable pharmaceutical formulations are described, for example, in "Pharmaceuticals—The Science of Dosage Form Design", M. B. Aulton, Churchill Livingstone, 1988.

A suitable daily dose for use in the treatment of any of the conditions mentioned above is within the range of 0.001 mg/kg to 10 mg/kg body weight, in particular within the range of 0.01 mg/kg to 5 mg/kg body weight, depending upon the specific condition to be treated, the age and weight of the specific patient, and the specific patient's response to the medication. The exact individual dosage, as well as the daily dosage, will be determined according to standard medical principles under the direction of a physician.

Various additives to enhance the stability or ease the administration of the drug can be added to the formulation. The pharmaceutical composition may also contain additional therapeutically useful substances other than one or more compounds of the general formula I.

The present invention is further illustrated by the following non-limiting experimental part.

Experimental Part

The compounds of general formula I may be prepared by the methods described below. The prior art patent documents cited above also include useful synthetic methods.

Thus, compounds of general formula I wherein Y=N and X is an alkyl chain can be prepared as shown in the reaction below;

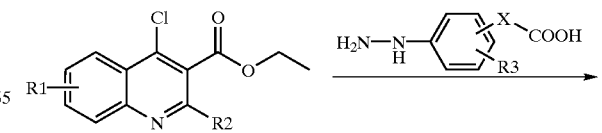

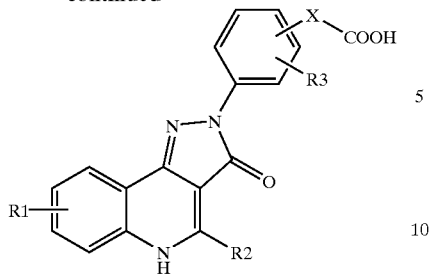

The starting material is available by known procedures (e.g. L. Savini et al, Bioorganic & Medicinal Chemistry 6 (1998) 389–399) and the reaction with hydrazine derivatives is performed by heating in a suitable solvent such as n-butanol. In cases where the acid is esterified under the reaction conditions, hydrolysis gives back the acid. Preparation of hydrazine derivatives was accomplished following literature procedures (Hunsberger et al, J. Org. Chem. 21 (1956) 394, 395, 396. Harden F. A. et al, J. Med. Chem. 34 (1991) 2892–8).

Compounds wherein R4 is lower alkyl may be obtained by subsequent alkylation. If the alkylation results in ester formation, the corresponding acid is easily obtained by hydrolysis.

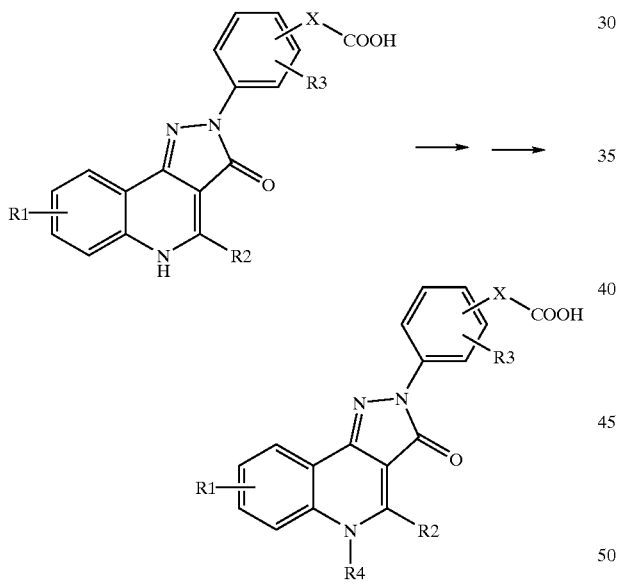

The compounds of general formula I wherein Y=O and X is an alkyl chain can be prepared according to various literature procedures (e.g. Ghosh C. K. Et al, Synthesis (1978) 779–781; Frogett J. A. et al, J. Chem. Research (S) (1997) 30–31). One synthetic route, when R2=Me, is described below. The cyano group is subsequently hydrolysed to produce the corresponding acid.

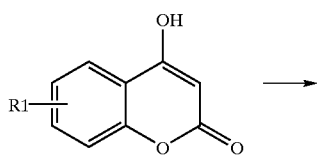

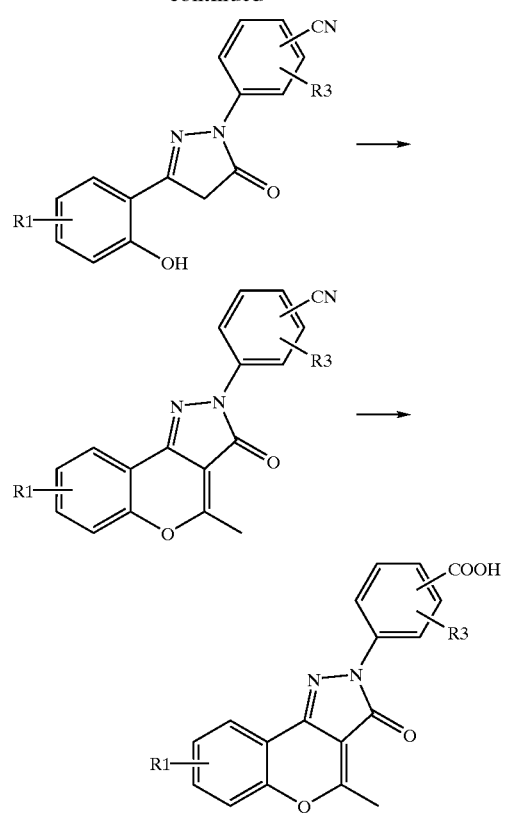

The compounds of general formula I wherein Y=S and X is an alkyl chain can be prepared as shown below using procedures described in the literature (Donelly M. X. D. et al, J. Chem. Soc. Perkin Trans. 1 (1993) 1729–1735; Lombardino J. G. et al, J. Med. Chem. 24 (1981) 830–834). The final oxidation was accomplished by stirring in air.

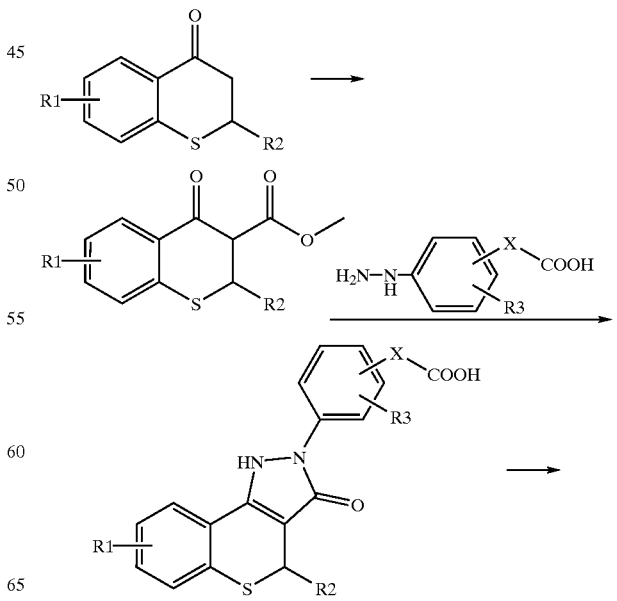

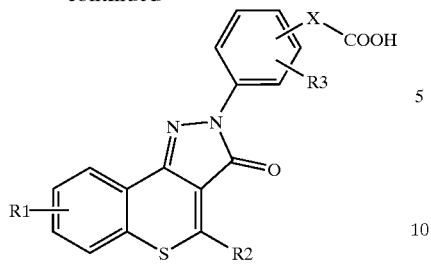

The compounds wherein X is a bond may also be obtained from the corresponding cyanide derivatives and the amino acid derivatives are prepared by condensation of the acid with the appropriate amino acid.

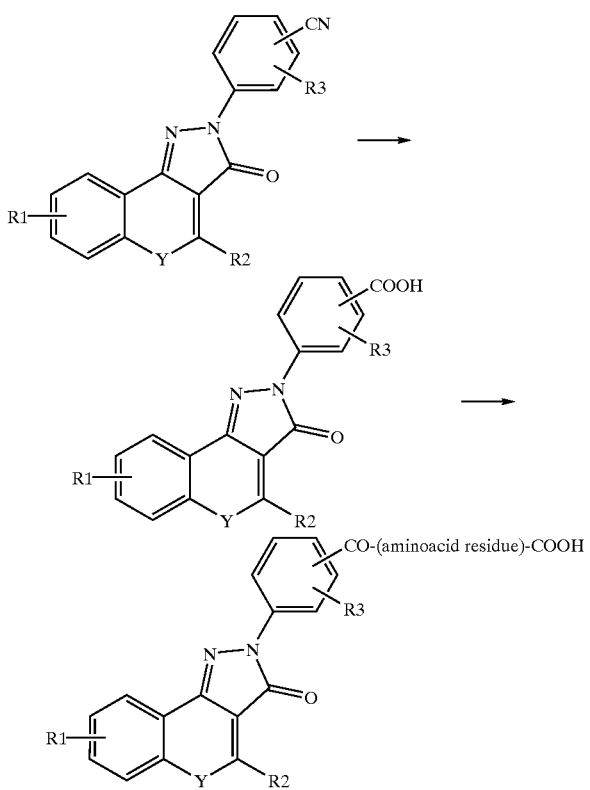

Compounds wherein X is NH—C(O)-(alkyl)- and NH—C(O)—CH$_2$—O—CH$_2$— can be prepared by reduction of the nitro group (L. Savini et al, Bioorganic & Medicinal Chemistry 6 (1998) 389–399) and subsequent acylation with the appropriate anhydride.

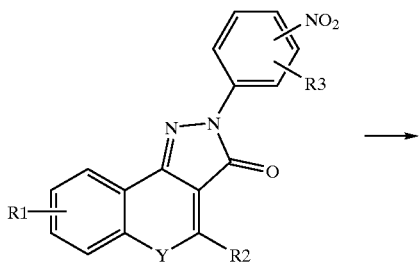

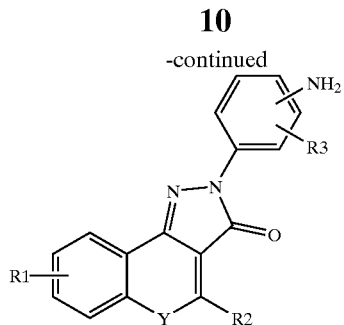

EXAMPLES

The following examples are intended to illustrate the invention without restricting the scope thereof. Compounds were named using Autonom 2.1 from Beilstein. NMR spectra were recorded on a Bruker ARX 400 instrument. Coupling constants in the aromatic area are mostly referred to as singlets (s), doublets (d), triplets (t) in order to reflect the appearance of the NMR spectrum.

Example 1
{[3-(3-Oxo-3,5-dihydro-pyrazolo[4,3-c]quinolin-2-yl)-phenylcarbamoyl]-methoxy}-acetic Acid To a suspension of 2-(3-amino-phenyl)-2,5-dihydro-pyrazolo[4,3-c]quinolin-3-one (0.050 g, 0.18 mmol) in DMF (0.8 ml) diglycolic anhydride (0.025 g, 0.22 mmol) and 4-dimethylaminopyridine (0.007 g, 0.05 mmol) were added. The clear solution was stirred at room temperature and the product precipitated during the reaction. After 3 h water was added to the mixture. The precipitate was collected, washed with water and dried to yield {[3-(3-oxo-3,5-dihydro-pyrazolo[4,3-c]quinolin-2-yl)-phenyl-carbamoyl]-methoxy}-acetic acid (0.064 g): $^1$H NMR (400 MHz, DMSO-d$_6$) δ 12.8 (1H, bs), 10.02 (1H, s), 8.69 (1H, s), 8.37 (1H, s), 8.18 (1H, d), 7.95 (1H, d), 7.62–7.70 (2H, m), 7.49–7.55 (2H, m), 7.33 (1H, t), 4.19 (2H, s), 4.17 (2H, s); ESI MS m/z 393 (M+H$^+$)

Using essentially the same procedure the following compounds were prepared:

N-[4-(3-Oxo-3,5-dihydro-pyrazolo[4,3-c]quinolin-2-yl)-phenyl]-succinamic Acid
$^1$H NMR (400 MHz, DMSO-d$_6$) δ 9.98 (1H, s), 8.67 (1H, s), 8.18 (1H, d), 8.08 (2H, d), 7.58–7.70 (4H, m), 7.51 (1H, t), 2.47–2.57 (4H, m); ESI MS m/z 377 (M+H$^+$).

4-[4-(3-Oxo-3,5-dihydro-pyrazolo[4,3-c]quinolin-2-yl)-phenylcarbamoyl]-butyric Acid
$^1$H NMR (400 MHz, DMSO-d$_6$) δ 9.89 (1H, s), 8.67 (1H, s), 8.18 (1H, d), 8.08 (2H, d), 7.60–7.69 (4H, m), 7.51 (1H, t), 2.33 (2H, t), 2.25 (2H, t), 1.75–1.83 (2H, m); ESI MS m/z 391 (M+H$^+$).

{[4-(3-Oxo-3,5-dihydro-pyrazolo[4,3-c]quinolin-2-yl)-phenylcarbamoyl]-methoxy}-acetic Acid
$^1$H NMR (400 MHz, DMSO-d$_6$) δ 12.76 (1H, bs), 9.86 (1H, s), 8.68 (1H, d), 8.19 (1H, d), 8.11 (2H, d), 7.61–7.69 (4H, m), 7.52 (1H, t), 4.19 (2H, s), 4.15 (2H, s); ESI MS m/z 393 (M+H$^+$).

4-[4-(3-Oxo-3,5-dihydro-pyrazolo[4,3-c]quinolin-2-yl)-phenylcarbamoyl]-2-phenyl-butyric Acid $^1$H NMR (400 MHz, DMSO-d$_6$) (contain some 3-phenyl regioisomer) δ 9.86 (1H, s), 8.67 (1H, s), 8.18 (1H, d), 8.07 (2H, d), 7.58–7.69 (4H, m), 7.51 (1H, t), 7.20–7.38 (5H, m), 3.55 (1H, t), 2.10–2.30 (3H, m), 1.90–2.02 (1H, m); ESI MS m/z 467 (M+H$^+$).

N-[3-(3-Oxo-3,5-dihydro-pyrazolo[4,3-c]quinolin-2-yl)-phenyl]-succinamic Acid $^1$H NMR (400 MHz, DMSO-d$_6$) δ 10.05 (1H, s), 8.68 (1H, s), 8.31 (1H, s), 8.17 (1H, d), 7.90 (1H, d), 7.62–7.70 (2H, m), 7.48–7.55 (2H, m) 7.30 (1H, t), 2.49–2.57 (4H, m) ESI MS m/z 377 (M+H$^+$)

2-{[4-(3-Oxo-3,5-dihydro-pyrazolo[4,3-c]quinolin-2-yl)-phenylcarbamoyl]-methyl}-benzoic Acid $^1$H NMR (400 MHz, DMSO-d$_6$) δ 10.11 (1H, s), 8.67 (1H, s), 8.18 (1H, d), 8.08 (2H, d), 7.85 (1H, d), 7.59–7.69 (4H, m), 7.46–7.54 (2H, m), 7.35 (2H, t), 4.07 (2H, s); ESI MS m/z 439 (M+H$^+$)

Example 2

4-(3-oxo-3,5-dihydro-pyrazolo[4,3-c]quinolin-2-yl)-benzoic Acid

A solution of 4-chloro-quinoline-3-carboxylic acid ethyl ester (11.8 mg, 0.5 mmol) and 4-hydrazino-benzoic acid (7.6 mg, 0.5 mmol) in n-butanol (0.5 mL) was stirred at 115° C. over night in a sealed tube. After cooling to 50–70° C., heptane (1.0 mL) was added and the product was allowed to crystallize upon further cooling to room temperature. The solvent was removed and the product was washed with heptane and dried under vacuum to yield 4-(3-oxo-3,5-dihydro-pyrazolo[4,3-c]quinolin-2-yl)-benzoic acid (13 mg). $^1$H NMR (400 MHz, DMSO-d$_6$) δ 12.9 (1H, s), 8.77 (1H, d), 8.38 (2H, d), 8.25 (1H, d), 8.03 (2H, d), 7.65–7.77 (2H, m), 7.58 (1H, t).

Using essentially the same procedure the following compounds were prepared:

3-(3-Oxo-3,5-dihydro-pyrazolo[4,3-c]quinolin-2-yl)-benzoic Acid $^1$H NMR (400 MHz, DMSO-d$_6$) δ 12.87 (1H, bs), 8.78 (1H, s), 8.72 (1H, d), 8.46 (1H, d), 8.23 (1H, d), 7.63–7.72 (3H, m), 7.51–7.56 (2H, m); ESI MS m/z 306 (M+H$^+$).

2-Chloro-4-(3-oxo-3,5-dihydro-pyrazolo[4,3-c]quinolin-2-yl)-benzoic Acid

In this reaction the hydrochloride salt of 2-chloro-4-hydrazino-benzoic acid was used and therefor Et$_3$N (2 eq) was also added to the mixture. $^1$H NMR (400 MHz, DMSO-d$_6$) δ 13.00 (1H, bs), 8.76 (1H, d), 8.44 (1H, s), 8.22–8.28 (2H, m), 7.94 (1H, d) 7.65–7.74 (2H, m), 7.55 (1H, t); ESI MS m/z 340 (M+H$^+$).

4-(6-Methyl-3-oxo-3,5-dihydro-pyrazolo[4,3-c]quinolin-2-yl)-benzoic Acid $^1$H NMR (400 MHz, DMSO-d$_6$) δ 12.1 (1H, s), 8.52 (1H, d), 8.38 (2H, d), 8.12 (1H, d), 8.03 (2H, d), 7.56 (1H, d), 7.48 (1H, t), 2.58 (3H, s).

4-(8-Methyl-3-oxo-3,5-dihydro-pyrazolo[4,3-c]quinolin-2-yl)-benzoic Acid $^1$H NMR (400 MHz, DMSO-d$_6$) δ 12.9 (1H, s), 8.73 (1H, d) 8.39 (2H, d), 8.06 (1H, s), 8.03 (2H, d), 7.64 (1H, d), 7.53 (1H, d), 2.50 (3H, s, in DMSO signal).

4-(6,8-Dimethyl-3-oxo-3,5-dihydro-pyrazolo[4,3-c]quinolin-2-yl)-benzoic Acid $^1$H NMR (400 MHz, DMSO-d$_6$) δ 8.48 (1H, s), 8.38 (2H, d), 8.03 (2H, d), 7.92 (1H, s), 7.40 (1H, s), 2.57 (3H, s), 2.45 (3H, s).

4-(8-tert-Butyl-3-oxo-3,5-dihydro-pyrazolo[4,3-c]quinolin-2-yl)-benzoic Acid $^1$H NMR (400 MHz, DMSO-d$_6$) δ 12.9 (1H, s), 8.75 (1H, d), 8.40 (2H, d), 8.17 (1H, s), 8.03 (2H, d), 7.81 (1H, d), 7.69 (1H, d), 1.40 (9H, s).

4-(8-Methoxy-6-methyl-3-oxo-3,5-dihydro-pyrazolo[4,3-c]quinolin-2-yl)-benzoic Acid $^1$H NMR (400 MHz, DMSO-d$_6$) δ 12.3 (1H, s), 8.45 (1H, d), 8.41 (2H, d), 8.03 (2H, d), 7.49 (1H, d), 7.21 (1H, d), 3.93 (3H, s), 2.57 (3H, s).

4-(8-Methoxy-3-oxo-3,5-dihydro-pyrazolo[4,3-c]quinolin-2-yl)-benzoic Acid $^1$H NMR (400 MHz, DMSO-d$_6$) δ 12.9 (1H, s), 8.71 (1H, d), 8.41 (2H, d), 8.03 (2H, d), 7.70 (1H, d), 7.61 (1H, d), 7.32 (1H, dd), 3.94 (3H, s).

4-(6,8-Dimethoxy-3-oxo-3,5-dihydro-pyrazolo[4,3-c]quinolin-2-yl)-benzoic Acid $^1$H NMR (400 MHz, DMSO-d$_6$) δ 8.40 (2H, d), 8.31 (1H, s) 8.03 (2H, d), 7.18 (1H, d), 6.93 (1H, d), 4.03 (3H, s), 3.95 (3H, s).

4-(7,9-Dimethoxy-3-oxo-3,5-dihydro-pyrazolo[4,3-c]quinolin-2-yl)-benzoic Acid $^1$H NMR (400 MHz, DMSO-d$_6$) δ 12.6 (s, 1H), 8.61 (1H, s) 8.36 (2H, d), 8.01 (2H, d), 6.79 (1H, d), 6.69 (1H, d), 4.00 (3H, s), 3.87 (3H, s).

4-(3-oxo-8-trifluoromethyl-3,5-dihydro-pyrazolo[4,3-c]quinolin-2-yl)-benzoic Acid (60% Pure by NMR)

$^1$H NMR (400 MHz, DMSO-d$_6$) δ 13.1 (1H, s), 8.85 (1H, d) 8.38 (2H, d), 8.10 (1H, s), 8.03 (2H, d), 7.87 (1H, d), 7.73 (1H, d).

4-(6-Fluoro-3-oxo-3,5-dihydro-pyrazolo[4,3-c]quinolin-2-yl)-benzoic Acid $^1$H NMR (400 MHz, DMSO-d$_6$) δ 13.0 (1H, s), 8.58 (1H, s), 8.37 (2H, d), 8.06 (1H, d), 8.04 (2H, d), 7.54–7.66 (2H, m).

4-(6-Chloro-3-oxo-3,5-dihydro-pyrazolo[4,3-c]quinolin-2-yl)-benzoic Acid $^1$H NMR (400 MHz, DMSO-d$_6$) δ 8.47 (1H, s), 8.36 (2H, d), 8.24 (1H, d), 8.04 (2H, d), 7.88 (1H, d), 7.57 (1H, t).

4-(8-Chloro-3-oxo-3,5-dihydro-pyrazolo[4,3-c]quinolin-2-yl)-benzoic Acid (85% Pure by NMR)

$^1$H NMR (400 MHz, DMSO-d$_6$) δ 13.0 (1H, s), 8.82 (1H, d), 8.38 (2H, d), 8.20 (1H, s), 8.03 (2H, d), 7.76 (2H, s).

4-(7,9-Dichloro-3-oxo-3,5-dihydro-pyrazolo[4,3-c]quinolin-2-yl)-benzoic Acid (60% Pure by NMR)

$^1$H NMR (400 MHz, DMSO-d$_6$) δ 13.0 (s, 1H), 8.81 (1H, s), 8.36 (2H, d), 8.04 (2H, d), 7.78 (1H, d), 7.71 (1H, d).

Example 3

[4-(3-Oxo-3,5-dihydro-pyrazolo[4,3-c]quinolin-2-yl)-phenyl]-propionic Acid

A suspension of 4-chloro-quinoline-3-carboxylic acid ethyl ester (0.050 g, 0.21 mmol) and 3-(4-hydrazino-phenyl)-propionic acid (0.046 g, 0.25 mmol) in 2-propanol (3 ml) was heated at 84° C. in an oil bath for 10 h. The precipitate was collected, washed with 2-propanol and dried to afford the 2-propylester of the product (0.031 g). $^1$H NMR (400 MHz, DMSO-d$_6$) δ 12.8 (1H, bs), 8.66 (1H, d), 8.18 (1H, d), 8.07 (2H, d), 7.60–7.72 (2H, m), 7.52 (1H, t), 7.26 (2H, d), 4.85 (1H, m), 2.82 (2H, t), 2.55 (2H, t), 1.12 (6H, d).

The ester (0.019 g) was hydrolysed by dissolving it in EtOH (0.8 ml) and 1M NaOH (0.4 ml). After 90 minutes the mixture was acidified with 2 M HCl and the precipitate was collected, washed with water and dried to yield [4-(3-oxo-3,5-dihydro-pyrazolo[4,3-c]quinolin-2-yl)-phenyl]-propionic acid (0.016 g): $^1$H NMR (400 MHz, DMSO-d$_6$) δ 8.66 (1H, s), 8.18 (1H, d), 8.07 (2H, d), 8.61–8.69 (2H, m), 7.51 (1H, t), 7.26 (2H, d), 2.81 (2H, t), 2.52 (2H, t); ESI MS m/z 334 (M+H$^+$).

Using essentially the same procedure the following compounds were prepared:

[4-(3-Oxo-3,5-dihydro-pyrazolo[4,3-c]quinolin-2-yl)-phenyl]-acetic Acid n-butyl Ester $^1$H NMR (400 MHz, DMSO-d$_6$) δ 12.8 (1H, bs), 8.68 (1H, d) 8.18 (1H, d), 8.13 (2H, d), 7.61–7–72 (2H, m), 7.53 (1H, t), 7.30 (2H, d), 4.02 (2H, t), 3.63 (2H, s), 1.52 (2H, m), 1.28 (2H, m), 0.83 (3H, t); and

[4-(3-Oxo-3,5-dihydro-pyrazolo[4,3-c]quinolin-2-yl)-phenyl]-acetic Acid $^1$H NMR (400 MHz, DMSO-d$_6$) δ 8.67 (1H, s), 8.19 (1H, d), 8.11 (2H, d), 7.61–7.69 (2H, m), 7.52 (1H, t), 7.29 (2H, d), 3.54 (2H, s); ESI MS m/z 320 (M+H$^+$).

Example 4

3-(4-Hydrazino-phenyl)-propionic Acid

A suspension of 3-(4-aminophenyl)-propionic acid (0.50 g, 3.0 mmol) in concentrated hydrochloric acid (3.5 ml) was treated with sodium nitrite (0.21 g, 3.0 mmol) in H$_2$O (1.7 ml) at 0° C. The reaction was stirred for 45 minutes after which stannous chloride (1.26 g, 6.7 mmol) in concentrated hydrochloride acid (1.5 ml) was added dropwise at 0° C. The reaction was stirred for 1 h at room temperature. The precipitate was collected and dried to afford the hydrochloride salt (0.54 g). The salt (0.100 g) was dissolved in a small amount of water and made basic with 1M NaOH. The solid material was removed by filtration and the filtrate was acidified with acidic acid to yield a precipitate. The solid was collected, washed with water and dried to afford 3-(4-hydrazino-phenyl)-propionic acid (0.050 g): $^1$H NMR (400 MHz, DMSO-d$_6$) δ 6.90 (2H, d), 6.64 (2H, d), 2.63 (2H, t), 2.39 (2H, t).

Using essentially the same procedure the following compound was prepared:

2-Chloro-4-hydrazino-benzoic Acid Hydrochloride

In this reaction the hydrochloride salt was collected and purified by recrystallization from ethanol: $^1$H NMR (400 MHz, DMSO-d$_6$) δ 8.97 (1H, bs), 7.76 (1H, d), 7.03 (1H, s), 6.88 (1H, d).

Example 5

4-[3-(2-Hydroxy-phenyl)-5-oxo-4,5-dihydro-pyrazolo-1-yl]-benzonitrile

A suspension of 4-hydroxycoumarine (0.71 g, 4.4 mmol) and 4-cyanophenylhydrazine (0.88 g, 6.6 mmol) in dry toluene was heated at 125° C. in an oil bath. Toluene was slowly distilled off during the reaction to separate water. A total of 30 ml toluene was removed. After 3 h the solution was allowed to cool and the precipitate was filtered, washed with toluene and dried. The crude product was dissolved in CH$_2$Cl$_2$. The solid material was removed by filtration before the solution was washed with 2M HCl. The organic phase was dried, filtrated and the solvent evaporated to yield 4-[3-(2-hydroxy-phenyl)-5-oxo-4,5-dihydro-pyrazolo-1-yl]-benzonitrile (0.44 g): $^1$H NMR (400 MHz, CDCl$_3$) δ 9.86 (1H, s), 8.01 (2H, d), 7.73 (2H, d), 7.41 (1H, t), 7.23–7.26 (1H, m), 7.08 (1H, d), 6.98 (1H, t), 3.99 (2H, s).

Example 6

4-(4-Methyl-3-oxo-3H-chromeno[4,3-c]pyrazol-2-yl)-benzonitrile

A mixture of 4-[3-(2-hydroxy-phenyl)-5-oxo-4,5-dihydro-pyrazolo-1-yl]-benzonitrile (0.25 g, 0.9 mmol) and triethyl orthoacetate (1.6 ml) was heated at 120° C. in an oil bath for 15 minutes. After cooling the precipitate was filtered, washed with diethyl ether and dried to yield 4-(4-methyl-3-oxo-3H-chromeno[4,3-c]pyrazol-2-yl)-benzonitrile (0.22 g): $^1$H NMR (400 MHz, CDCl$_3$) δ 8.35 (2H, d), 8.18 (1H, d), 7.70 (2H, d), 7.58–7.62 (1H, m), 7.47–7.51 (2H, m), 2.84 (3H, s); ESI MS m/z 302 (M+H$^+$)

Example 7

4-(4-Methyl-3-oxo-3H-chromeno[4,3-c]pyrazol-2-yl)-benzoic Acid

A mixture of 4-(4-methyl-3-oxo-3H-chromeno[4,3-c]pyrazol-2-yl)-benzonitrile (0.030 g, 0.10 mmol), acetic acid (0.4 ml), H$_2$SO$_4$ (0.4 ml) and water (0.4 ml) was heated at 100° C. in an oil bath for 19 h. After cooling water was added and the precipitation collected, washed with water and dried to yield 4-(4-methyl-3-oxo-3H-chromeno-[4,3-c]pyrazol-2-yl)-benzoic acid (0.029 g): $^1$H NMR (400 MHz, DMSO-d$_6$) δ 8.21 (2H, d), 8.13 (1H, d), 8.01 (2H, d), 7.67–7.75 (2H, m), 7.54–7.58 (1H, m), 2.78 (3H, s); ESI MS m/z 321 (M+H$^+$).

Using essentially the same procedure the following compound was prepared:

4-(3-Oxo-3H-thiochromeno[4,3-c]pyrazol-2-yl)benzoic Acid:

$^1$H NMR (400 MHz, DMSO-d$_6$) δ 9.29 (1H, s), 8.44 (1H, d), 8.24 (2H, d), 8.03 (2H, d), 7.98 (1H, d), 7.67–7.76 (2H, m); ESI MS m/z 323 (M+H$^+$).

Example 8

4-Oxo-thiochroman-3-carboxylic Acid Methyl Ester

LHMDS (1.12 g, 6.7 mmol) dissolved in anhydrous THF (7 ml) was cooled to −78° C. under N$_2$. Thiochroman-4-one (1.00 g, 6.1 mmol) in anhydrous THF (20 ml) was added dropwise under 20 minutes. After an additional 60 minutes methyl cyanoformate (0.62 g, 7.3 mmol) in anhydrous THF (1.5 ml) was added dropwise under 5 minutes and the suspension was then stirred at −78° C. for 80 minutes. The suspension was poured onto 10% NH$_4$Cl and extracted with ether. The organic phase was washed with water, dried (Na$_2$SO$_4$), filtered and the solvent evaporated. The crude product was purified by chromatography on silica gel (heptane-ethyl acetate 10:1) to yield 4-oxo-thiochroman-3-carboxylic acid methyl ester (0.65 g): $^1$H NMR (400 MHz, CDCl$_3$; enol tautomer) δ 12.64 (1H, s), 7.83 (1H, d), 7.25–7.29 (2H, m), 7.16–7.20 (1H, m), 3.84 (3H, s), 3.71 (2H, s).

Example 9

4-(3-Oxo-1,4-dihydro-3H-thiochromeno[4,3-c]pyrazol-2-yl)-benzonitrile

4-Oxo-thiochroman-3-carboxylic acid methyl ester (0.200 g, 0.90 mmol), 4-cyanophenylhydrazine (0.132 g, 0.99 mmol) together with a small amount of pivalic acid was heated at 118° C. in an oil bath under N$_2$. After 1 h the mixture was cooled to room temperature and then triturated with ether. The precipitate was filtered and dried to yield 4-(3-oxo-1,4-dihydro-3H-thiochromeno[4,3-c]pyrazol-2-yl)-benzonitrile (0.233 g): $^1$H NMR (400 MHz, DMSO-d$_6$) δ 8.06 (2H, d), 7.92 (2H, d), 7.80–7.83 (1H, m), 7.30–7.33 (1H, m), 7.18–7.25 (2H, m), 3.91 (2H, s).

Example 10

4-(3-Oxo-3H-thiochromeno[4,3-c]pyrazol-2-yl)-benzonitrile

A solution of 4-(3-oxo-1,4-dihydro-3H-thiochromeno[4, 3-c]pyrazol-2-yl)-benzonitrile (0.100 g, 0.33 mmol) in DMSO (2 ml) was stirred vigorously at room temperature and air was flushed over the solution. After 48 h the precipitation was filtered, washed with toluen and dried. The crude product recrystallized from toluene to yield 4-(3-oxo-3H-thiochromeno[4,3-c]pyrazol-2-yl)-benzonitrile (0.036 g): $^1$H NMR (400 MHz, CDCl$_3$) δ 8.65 (1H, s), 8.53 (1H, d), 8.38 (2H, d), 7.72 (2H, d), 7.66 (2H, t), 7.58–7.62 (1H, m); ESI MS m/z 304 (M+H$^+$).

Example 11

4-(5-Methyl-3-oxo-3,5-dihydro-pyrazolo [4,3-c]quinolin-2-yl)-benzoic Acid

A suspension of 4-(3-oxo-3,5-dihydro-pyrazolo[4,3-c]quinolin-2-yl)-benzoic acid (0.050 g, 0.16 mmol) in DMF (1 ml) was added in small portions to a suspension of NaH (55%) (0.017 g, 0.39 mmol) in DMF (0.5 ml) under N$_2$. The reaction was stirred at room temperature. After 1 h MeI (0.053 g, 0.38 mmol) was added. After additional 24 h water was added and the solid material (mainly consisting of ester product) was removed by filtration. The filtrate was acidified with 2M HCl. The precipitate was collected, washed with water and dried to yield 4-(5-methyl-3-oxo-3,5-dihydro-pyrazolo[4,3-c]quinolin-2-yl)-benzoic acid (0.018 g). This material contained approx. 10% of ester product: $^1$H NMR (400 MHz, DMSO-d$_6$) δ 8.89 (1H, s), 8.34 (2H, d), 8.29 (1H, d), 7.99 (2H, d), 7.85 (1H, d), 7.76 (1H, t), 7.62 (1H, t), 4.00 (3H, s); ESI MS m/z 320 (M+H$^+$).

Example 12

2-[4-(3-Oxo-3,5-dihydro-pyrazolo[4,3-c]quinolin-2-yl)-benzoylamino]-3-phenyl-propionic Acid 4-(3-Oxo-3,5-dihydro-pyrazolo[4,3-c]quinolin-2-yl)-benzoic acid (30 mg, 0.1 mmol) was dissolved in DMF (0.5 ml) and 18 mg (0.1 mmol) of carbonyldiimidazol (90% pure) was added and the mixture stirred for 4 h. Phenylalanine (33 mg, 0.2 mmol) was dissolved in of H$_2$O (0.5 ml) together with triethylamine (0.05 ml) and added to the activated acid. This reaction mixture was heated at 75° C. for 2 h. After cooling it was made acidic and diluted 5×with H$_2$O. The precipitate was filtered and washed with H$_2$O and dried under vacuum. FlashTube chromatography using EtOAc/MeOH(7:3) yielded a small amount of 2-[4-(3-Oxo-3,5-dihydro-pyrazolo[4,3-c]quinolin-2-yl)-benzoylamino]-3-phenyl-propionic acid. The material contained approx. 10% of starting material. $^1$H NMR (400 MHz, DMSO-d$_6$) δ 8.7 (1H, s), 8.31 (2H, d), 8.21 (1H, d), 7.82 (2H, d), 7.70 (1H, d), 7.62 (1H, t), 7.50 (1H, t), 7.2–7.3(4H, m), 7.17 (1H, t), 4.50 (1H, m), 3.1–3.2 (2H,m).

Using essentially the same procedure the following compound was prepared:

2-[4-(3-Oxo-3,5-dihydro-pyrazolo[4,3-c]quinolin-2-yl)-benzoylamino]-2-acetic Acid $^1$H NMR (400 MHz, DMSO-d$_6$) δ 8.7 (1H, s), 8.36 (2H, d), 8.22 (1H, d), 7.92 (2H, d), 7.70 (1H, d), 7.63 (1H, t) 7.51 (1H, t), 3.85 (2H,d)

Example 13

Time resolved fluorescence competition assay protocol: CD28–CD80 interactions.

| Reagent | Supplier |
| --- | --- |
| Eu-labelled anti-Rabbit antibody (αR-Eu) | Wallac Oy, Turku, Finland, |
| Rabbit anti-mouse IgG, Fc fragment specific (RαmIg (Fc)) | Jackson Immunoresearch Laboratories Inc., |
| Human CD28-mouse IgG1 (Fc) (CD28-mFc) | Active Biotech Research AB |
| Human CD80-mouse C215 Fab (C215Fab-hCD80) | Active Biotech Research AB |
| Mouse C215Fab | Active Biotech Research AB |
| Biotin conjugated Goat anti-mouse IgG Kappa light chain (GαMk-biot) | Southern Biotechnology Ass. Inc. |
| Streptavidin-allophycocyanin (SA-APC) | Wallac Oy, Turku, Finland |

Assay Buffer 50 mM Tris-HCl, 150 mM NaCl, 0.05% Tween 20, pH 7.8, containing 0.1% BSA (w/v), added prior to use.

Sample Preparation

The substances to be tested for inhibitory effects were serially diluted from stock concentrations of 20 mM (DMSO) in assay buffer to preparation concentrations of 200, 100, 50 and 25 μM. The final concentration in the wells was 100, 50, 25 and 12.5 μM, respectively. The maximum final DMSO concentration tolerated in the assay was 0.5%. Where appropriate, the dilution series was adjusted and extended to measure the IC$_{50}$.

Control

CTLA4-hIg(Fc) was diluted to working concentrations of 20 nM and 2 nM, resulting in final concentrations of 10 nM and 1 nM in the well. At these concentrations (10 nM and 1 nM) approximately 90% and 30% inhibition levels were observed.

Preparation of Reagent Mixture

For 1 plate:

To a tube containing 1.1 ml assay buffer, the following reagents were added:

| Reagent | Volume/1.1 ml assay buffer | Preparation conc | Final conc in well |
| --- | --- | --- | --- |
| αR-Eu | 4.2 μl from 0.528 mg/ml | 2 μg/ml | 1 μg/ml |
| RαmFc | 2.8 μl from 2.4 mg/ml | 6 μg/ml | 3 μg/ml |
| CD28-mFc | 2.6 μl from 0.4 mg/ml | 0.95 μg/ml (10 nM) | 0.48 μg/ml (5 nM) |
| Gαmk-biotin | 8.8 μl from 0.5 mg/ml | 4 μg/ml | 2 μg/ml |
| SA-APC | 15.4 μl from 1 mg/ml | 16 μg/ml | 8 μg/ml |

CD80FabC215 Mixture

900 μl of the above reagent mixture was transferred to a new tube. CD80FabC215 was added at a preparation concentration of 20 nM, (i.e. 4.3 μl from 0.4 mg/ml stock). The final concentration in the well was 10 nM.

FabC215 Mixture

To the remaining 200 μl reagent mixture C215Fab was added as control for non-specific binding (NSB). 0.5 μl from a 0.36 mg/ml stock gave a preparation concentration of 20 nM and a final concentration in the well of 10 nM.

Pipetting

To a black, half area, 96-well microtiter plate, the C215Fab containing reagent mixture was transferred to column 12, row E–H (4 wells), 10 μl/well with a single channel electronic pipette. 10 μl/well of the CD80FabC215 containing reagent mixture was transferred with a single channel electronic pipette to all other wells on the plate B0: Assay buffer, 10 μl/well was pipetted to the CD80FabC215 containing wells in column 12, row A–D (4 wells).

NSB: Assay buffer, 10 μl/well was pipetted to the C215Fab containing wells in column 12, row E–H (4 wells).

CTLA4-hIg(Fc), 10 μl/well of 20 and 2 nM (final conc 10 and 1 nM) was pipetted in duplicate into well 11 E–F and 11 G–H.

Sample dilution series: 10 μl/well in duplicate to the remaining wells.

Incubation

The plate was covered with a plastic lid and incubated in the dark: Initially for 1 h on a shaker platform at room temperature (RTS), stationary at +4° C. overnight, and finally 1 h RTS before reading.

Measurement

The plate was measured on a Victor 1420 Multilabel Counter using the LANCE protocol (#2) measuring emission at dual wavelengths, from both APC (665 nm) and Europium (615 nm). First measurement: Excitation 340 nm, emission 665 nm, delay 50 μs, window time 200 μs. Second measurement: Excitation 340 nm, emission 615 nm, delay 50 μs, window time 200 μs.

Calculation

The fluorescence signal ratio 1000* 665 nm/615 nm, from which the percentage inhibition was calculated, was determined. A logit b plot (Logit b=LN (% Bound/(100% -% Bound, plotted against Log conc) was performed from which $IC_{50}$ was measured.

The assay was performed at least twice in order to have two comparable $IC_{50}$ values of the compounds.

Results

The following representative results were obtained:

4-(3-oxo-3,5-dihydro-pyrazolo[4,3-c]quinolin-2-yl)-benzoic acid
$IC_{50}$=0.48 μM
2-Chloro-4-(3-oxo-3,5-dihydro-pyrazolo[4,3-c]quinolin-2-yl)-benzoic acid
$IC_{50}$=0.27 μM
3-(3-Oxo-3,5-dihydro-pyrazolo[4,3-c]quinolin-2-yl)-benzoic acid
$IC_{50}$=0.88 μM
N-[4-(3-Oxo-3,5-dihydro-pyrazolo[4,3-c]quinolin-2-yl)-phenyl]-succinamic acid
$IC_{50}$=0.6 μM
[4-(3-Oxo-3,5-dihydro-pyrazolo[4,3-c]quinolin-2-yl)-phenyl]-propionic acid
$IC_{50}$=1.6 μM
2-[4-(3-Oxo-3,5-dihydro-pyrazolo[4,3-c]quinolin-2-yl)-benzoylamino]-2-acetic acid
$IC_{50}$=3.9 μM
4-(3-Oxo-3H-thiochromeno[4,3-c]pyrazol-2-yl)benzoic acid
$IC_{50}$=13.5 μM

What is claimed is:

1. A compound having the general formula (I)

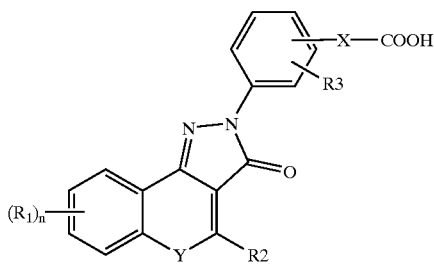

wherein X represents a bond or a group selected from substituted or unsubstituted $C_{1-3}$-alkyl, NH—C(O)—$C_{1-3}$-alkyl, NH—C(O)—$CH_2$—O—$CH_2$, or C(O)—NH—C(Z)H wherein Z represents side chains in naturally occurring amino acids;

Y represents NR4, O or

R1 represents halo, $CF_3$, lower alkyl or lower alkoxy;

n is an integer from 0 to 2;

R2 and R4 represents independently H or lower alkyl; and

R3 represents H, halo, lower alkyl or lower alkoxy, wherein halo is F, Cl or Br;

wherein lower alkyl represents saturated or unsaturated, straight, branched or cyclic alkyl groups having 1–6 carbon atoms; and wherein lower alkoxy represents saturated or unsaturated, straight, branched or cyclic alkoxy groups having 1–6 carbon atoms, with the proviso that R2 is not H, when X is a bond, Y is NH and R3 is H, or pharmaceutically acceptable salts thereof.

2. A compound according to claim 1, wherein X is a bond.

3. A compound according to claim 1, wherein Y is NH.

4. A compound according to claim 1, selected from the group consisting of

{[3-(3-Oxo-3,5-dihydro-pyrazolol[4,3-c]quiuolin-2-yl)-phenylcarbamoyl]-methoxy}-acetic acid, N-[4-(3-Oxo-3,5-dihydro-pyrazolo[4,3-c]quinolin-2-yl)-phenylcarbamoyl]-butyric acid, {[4-(3-Oxo-3,5-dihydro-pyrazclo[4,3-c]quinolin-2-yl)-phenylcarbamoyl]-methoxy}-acetic acid, 4-[4-(3-Oxo-3,5-dihydro-pyrazolo[4,3-c]quinolin-2-yl)-phenylcarbamoy]-2-phenyl-butyric acid, N-[3-(3-Oxo-3,5-dihydro-pyrazolo[4,3-c]quinolin-2-yl)phenyl]succinamic acid, 2-{[4(3-Oxo-3,5-dihydro-pyrazolo[4,3-c]quinolin-2-yl)-phenylcarbamoyl]-methyl}-benzoic acid, 2-Chloro-4-(3-oxo-3,5-dihydro-pyrazolo[4,3-c]quinolin-2-yl)-benzoic acid,

[4-(3-Oxo-3,5-dihydro-pyrazolo[4,3-c]quinolin-2-yl)phenyl]-propionic acid,

[4-(3-Oxo-3,5-dihydro-pyrazolo[4,3-c]quinolin-2-yl)-phenyl]-acetic acid, 4-(4-Methyl-3-oxo-3H-chromeno[4,3-c]pyrazol-2-yl)-benzoic acid, 4-(3-Oxo-3H-thiochromeno[4,3-c]pyrazol-2-yl)-benzoic acid, 4-(5-Methyl-3-oxo-3,5-dihydro-pyrazolo[4,3-c]quinolin-2-yl)-benzoic acid, 2-[4-(3-Oxo-3,5-dihydro-pyrazolo[4,3-c]quinolin-2-yl)-benzoylamino]-3-phenyl-propionic acid, and 2-[4-(3-Oxo-3,5-dihydro-pyrazolo[4,3-c]quinolin-2-yl)-benzoylamino]-2-acetic acid.

5. A method of inhibiting interaction between CD80 and CD2S comprising administering to a subject a therapeutically effective amount of a compound according to claim 1.

6. A pharmaceutical composition comprising a compound according to claim 1 as active ingredient in association with a pharmaceutically acceptable adjuvant, diluent or carrier.

7. A pharmaceutical composition according to claim 6 for treatment of medical conditions chosen from the group consisting of rheumatoid arthritis, multiple sclerosis, diabetes, asthma, transplantation, systemic lupus erythematosis and psoriasis.

8. A method for treatment of medical conditions which benefit from a CD80 antagonist comprising administration to a patient in need thereof of a therapeutically effective amount of a compound having the general formula (I)

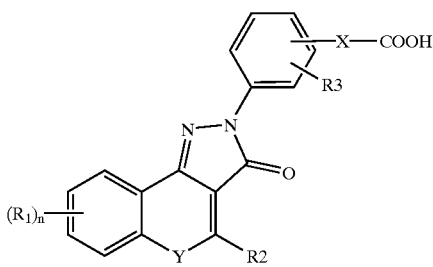

wherein X represents a bond or a group selected from substituted or unsubstituted $C_{1-3}$-alkyl, NH—C(O)—$C_{1-3}$-alkyl, NH—C(O)—CH$_2$—O—CH$_2$, or C(O)—NH—C(Z)H wherein Z represents side chains in naturally occurring amino acids;

Y represents NR4, O or S;

R1 represents halo, CF$_3$, lower alkyl or lower alkoxy;

n is an integer from 0 to 2;

R2 and R4 represents independently 1–1 or lower alkyl; and

R3 represents H, halo, lower alkyl or lower alkoxy, wherein halo is F, Cl or Br;

wherein lower alkyl represents saturated or unsaturated, straight, branched or cyclic alkyl groups having 1–6 carbon atoms; and wherein lower alkoxy represents saturated or unsaturated, straight, branched or cyclic alkoxy groups having 1–6 carbon atoms, or pharmaceutically acceptable salts thereof.

9. A method according to claim 8, wherein said medical conditions are chosen from the group consisting of rheumatoid arthritis, multiple sclerosis, diabetes, asthma, transplantation, systemic lupus erythematosis and psoriasis.

10. A method according to claim 8, wherein said therapeutically effective amount per day is within the range of 0.001–10 mg/kg body weight.

11. A compound according to claim 2, wherein Y is NH.

12. A method of inhibiting interaction between CD80 and CD28 comprising administering to a subject a compound according to claim 2 in an amount effective for said inhibition.

13. A method of inhibiting interaction between CD80 and CD28 comprising administering to a subject a compound according to claim 3 in an amount effective for said inhibition.

14. A method of inhibiting interaction between CD80 and CD28 comprising administering to a subject a compound according to claim 4 in an amount effective for said inhibition.

15. A method of inhibiting interaction between CD80 and CD28 comprising administering to a subject a compound according to claim 11 in an amount effective for said inhibition.

16. A pharmaceutical composition comprising a compound according to claim 2 as active ingredient in association with a pharmaceutically acceptable adjuvant, diluent or carrier.

17. A method according to claim 9, wherein said therapeutically effective amount per day is within the range of 0.001–10 mg/kg body weight.

18. A compound according to claim 1, wherein Y is O.

19. A compound according to claim 1, wherein Y is S.

20. A compound selected from the group consisting of
4-(6,8-Dimethyl-3-oxo-3,5-dihydro-pyrzolo[4,3-c]quinolin-2-yl)-benzoic acid,
4-(8-Methoxy-6-methyl-3-oxo-3,5-dihydro-pyrazolo[4,3-c]quinolin-2-yl)-benzoic acid,
4-(6,8-Dimethoxy-3-oxo-3,5-dihydro-pyrazolo[4,3-c]quinolin-2-yl)-benzoic acid,
4-(7,9-Dimethoxy-3-oxo-3,5-dihydro-pyrazolo[4,3-c]quinolin-2-yl)-benzoic acid,
4–6-Methyl-3-oxo-8-trifluoromethyl-3,5-dihydro-pyrazola[4,3-c]quinolin-2-yl)-benzoic acid,
4-(7,9-Dichloro-3-oxo-3,5-dihydro-pyrazolo[4,3-c]quinolin-2-yl)-benzoic acid, and pharmaceutically acceptable salts thereof.

21. The method of claim 10, wherein the therapeutically effective amount per day is within the range of 0.1–5 mg/kg body weight.

22. The method of claim 17, wherein the therapeutically effective amount per day is within the range of 0.1–5 mg/kg body weight.

* * * * *

UNITED STATES PATENT AND TRADEMARK OFFICE
CERTIFICATE OF CORRECTION

PATENT NO. : 6,642,249 B2
DATED : November 4, 2003
INVENTOR(S) : Per Axel Bjork et al.

It is certified that error appears in the above-identified patent and that said Letters Patent is hereby corrected as shown below:

Title page,
Item [75], Inventors, please delete "Pous" and insert therefore -- Poul --.
Item [57], ABSTRACT,
Line 2, please delete "comprisining" and insert therefore
-- comprising --.

Column 18,
Line 23, please delete "Y represents NH4, O or" and insert therefore
-- Y represents NH4, O or S --.
Line 24, please delete "quiuolin-2-yl" and insert therefore -- quinolin-2-yl --.
Line 24, please insert -- N-[4-(3-Oxo-3,5-dihydro-pyrazolo[4,3-*c*]quinolin-2-yl)-phenyl]-succinamic acid, --.
Line 27, please delete "pyrazclo" and insert therefore -- pyrazolo --.
Line 30, please delete "phenylcarbamoy" and insert therefore -- phenylcarbamoyl --.
Line 54, please delete "CD2S", and insert therefore -- CD28 --.

Column 19,
Line 23, please delete "1-1", and insert therefore -- H --.

Column 20,
Line 23, please delete "pyrzolo" and insert therefore -- pyrazolo --.
Line 32, please delete "dihydro-pyrazola", and insert therefore -- dihydro-pyrazolo --.

Signed and Sealed this

Twentieth Day of April, 2004

JON W. DUDAS
*Acting Director of the United States Patent and Trademark Office*